United States Patent [19]

Schmid

[11] Patent Number: 4,548,713
[45] Date of Patent: Oct. 22, 1985

[54] PULSE DAMPER

[75] Inventor: Carl E. Schmid, Easton, Conn.

[73] Assignee: The Perkin-Elmer Corporation, Norwalk, Conn.

[21] Appl. No.: 585,664

[22] Filed: Mar. 2, 1984

[51] Int. Cl.[4] ............................................. B01D 15/08
[52] U.S. Cl. .................................. 210/198.2; 210/349; 417/540
[58] Field of Search ............................. 210/198.2, 349; 417/540–543

[56] References Cited

U.S. PATENT DOCUMENTS

| | | | |
|---|---|---|---|
| 3,804,125 | 4/1974 | Sonneman | 417/540 |
| 3,851,661 | 12/1974 | Fernandez | 417/540 |
| 4,132,511 | 1/1979 | Boehme et al. | 417/540 |
| 4,427,029 | 1/1984 | Charnet et al. | 210/198.2 |

Primary Examiner—John Adee
Attorney, Agent, or Firm—J. D. Crane; F. L. Masselle; E. T. Grimes

[57] ABSTRACT

A pulse damper for use in a liquid chromatographic solvent delivery system includes a cavity within a housing containing a compliant medium. The compliant medium being an elastomer. As a consequence, a solvent flow volume can be precisely formed and maintained.

13 Claims, 3 Drawing Figures

PULSE DAMPER

BACKGROUND OF THE INVENTION

The present invention generally relates to a pulse damper for a liquid chromatographic solvent delivery system and, in particular, relates to such a pulse damper having an elastomer as a compliant medium.

In the analysis of a sample via liquid chromatography the sample solution is injected into a solvent stream which carries the sample through a chromatographic separating column. Conventionally, the solvent is introduced into a piston cylinder, for example, by the withdrawal stroke of a piston, from a solvent reservoir and delivered to an injector and column by the extension stroke of the piston. For reasons well known in the art, sharp pressure changes, i.e., pulses, occur between each piston cycle, which pulses are detrimental to the chromatographic analysis. Consequently, considerable time and effort has been expended to reduce the sharpness of these pressure changes. As a result, most single piston pumps in liquid chromatography instruments include a pulse damper serially connected in the solvent delivery conduit.

Conventional pulse dampers store pressure via a spring or by a compressible fluid or gas, usually air or methanol. In the case of a fluid or gas the compliant medium is stored in a reservoir, and, being confined, is pressure absorbent and thus reduces the magnitude of the solvent pressure variations. Typical pulse dampers utilize either a metal or a PTFE (polytetrafluroethelene) diaphragm to isolate the solvent from the compliant medium.

These pulse dampers have a number of disadvantages, the major one of which is that the compliant medium must be completely sealed, i.e., no leakage whatsoever thereof is permitted. If any leakage occurs the volume allowed for solvent flow increases and subsequently overstretches the diaphragm resulting in the rupture thereof.

Another disadvantage is the precision required in loading the compliant medium. For instance, in liquid chromatography it is preferred that the solvent clearance volume be small. However, if this volume is too small, thermal expansion of the compliant medium expands the diaphragm into the solvent ports, thereby rupturing the diaphragm. If the solvent clearance volume is too large, the volume limits the solvent composition transition volume. In addition, because the solvent clearance is small and the diaphragm is quite close to the solvent ports, if the solvent pressure is abruptly relieved a shockwave occurs in the compliant medium which often forces the diaphragm to rupture against a port.

Yet another disadvantage, which is particularly acute when methanol is the compliant medium, is that methanol swells conventionally compatible "O-ring" materials and thus requires the use of a more expensive spring loaded PTFE seal which includes a metal spring. However, the use of such a seal in conjunction with the typical aluminum housing causes electrolytic pitting of the aluminum and hence forces the use of a more expensive stainless steel housing.

Finally, any failure requires an elaborate refilling procedure to refurbish the failed unit.

SUMMARY OF THE INVENTION

Accordingly, it is one object of the present invention to provide a pulse damper which substantially completely overcomes the above-recited disadvantages.

This object is accomplished, at least in part, by a pulse damper having an elastomer as a compliant medium.

Other objects and advantages will become apparent to those skilled in the art from the following detailed description read in conjunction with the appended claims and the drawing attached hereto.

BRIEF DESCRIPTION OF THE DRAWING

The drawing, which is not drawn to scale, includes.

DETAILED DESCRIPTION OF THE INVENTION

Figure 1:
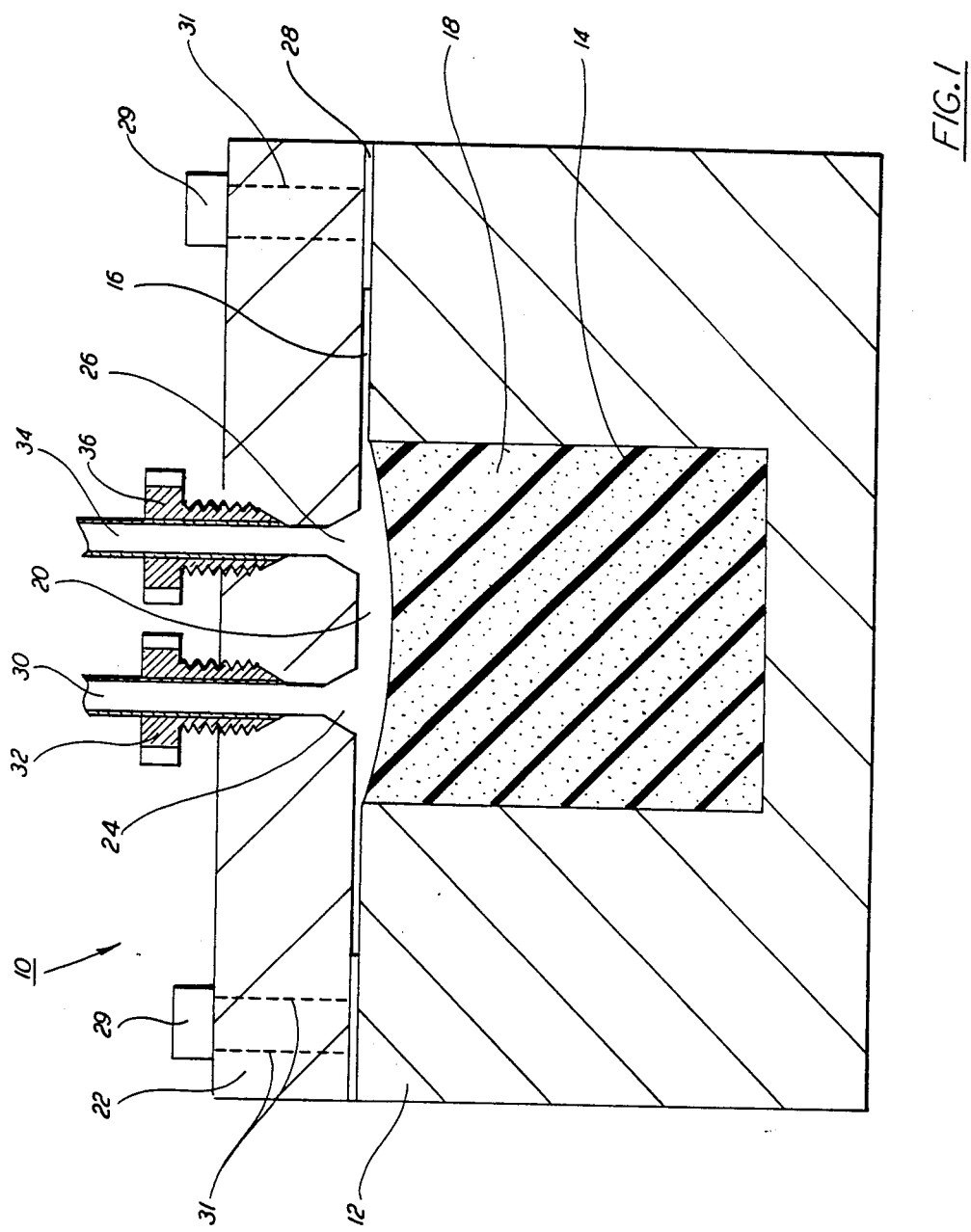
FIG. 1, which is a cross-sectional view of a pulse damper embodying the principles of the present invention.

A pulse damper assembly, generally indicated at 10 in FIG. 1 and embodying the principles of the present invention, includes a housing 12 defining a cavity 14 therein, which cavity 14 extends into the housing 12 from a first surface 16 thereof. The cavity 14 is substantially completely filled with a compliant medium 18 which is an elastomer, whereby a solvent flow volume 20 remains between the compliant medium 18 and the plane of the first surface 16. The assembly 10 further includes a cover 22 overlying and affixed to the first surface 16 of the housing 12. The cover 22 includes a solvent inlet means 24 and a solvent outlet means 26. The solvent inlet and outlet means, 24 and 26, respectively, open onto the solvent flow volume 20. In addition, a compressible gasket 28 is provided between the cover 22 and housing 12 to prevent solvent leakage during operation. The assembly 10 also includes means 29 for retaining the cover 22 to the housing 12, which means 29 are, for example, conventional bolts threaded into the housing 12 via clearance holes 31 in the cover 22.

In this embodiment, the cavity 14 has a cross-sectional diameter of about 3.8 cm. and extends into the housing 12 a distance of about 2.5 cm. from the first surface 16. The gasket 28 is annular with an inside diameter slightly greater than the diameter of the cavity 14 and formed from polytetrafluroethelene (PTFE).

In the preferred embodiment, the compliant medium 18 is RTV3110, an elastomer manufactured and marketed by Dow Chemical Corporation. The compliant medium 18 is formed in the cavity 14 and, during the setting thereof, the concave solvent flow volume 20 is formed. Alternatively, the compliant medium 18 can be preformed and subsequently inserted into the cavity 14. Preferably, the solvent flow volume 20 is formed by placing a spherical surface of a plano-convex lens thereupon during the curing time. In one embodiment, the plano-convex lens has a radius of curvature of about 15 cm and thus forms an uncompressed solvent flow volume 20 of about 825 microliters.

In operation, an inlet conduit 30 is interfaced with the solvent inlet means 26 via a conventional fitting 32 and an outlet conduit 34 interfaces with the solvent outlet means 26 via another conventional fitting 36. Consequently, solvent being delivered to a chromatographic separating column from the pump, passes through the solvent flow volume 20, which solvent clearance volume 20 varies due to the variation in pressure. Consequently, as an energy storage mechanism, the compliant medium 18, via pressure from the solvent, absorbs excess pressures and reduces the solvent flow volume 20 by expansion when that pressure is removed. Thus, the solvent flow through the outlet conduit 34 exhibits less perturbations by the pulses caused by the solvent pump.

Figure 2:
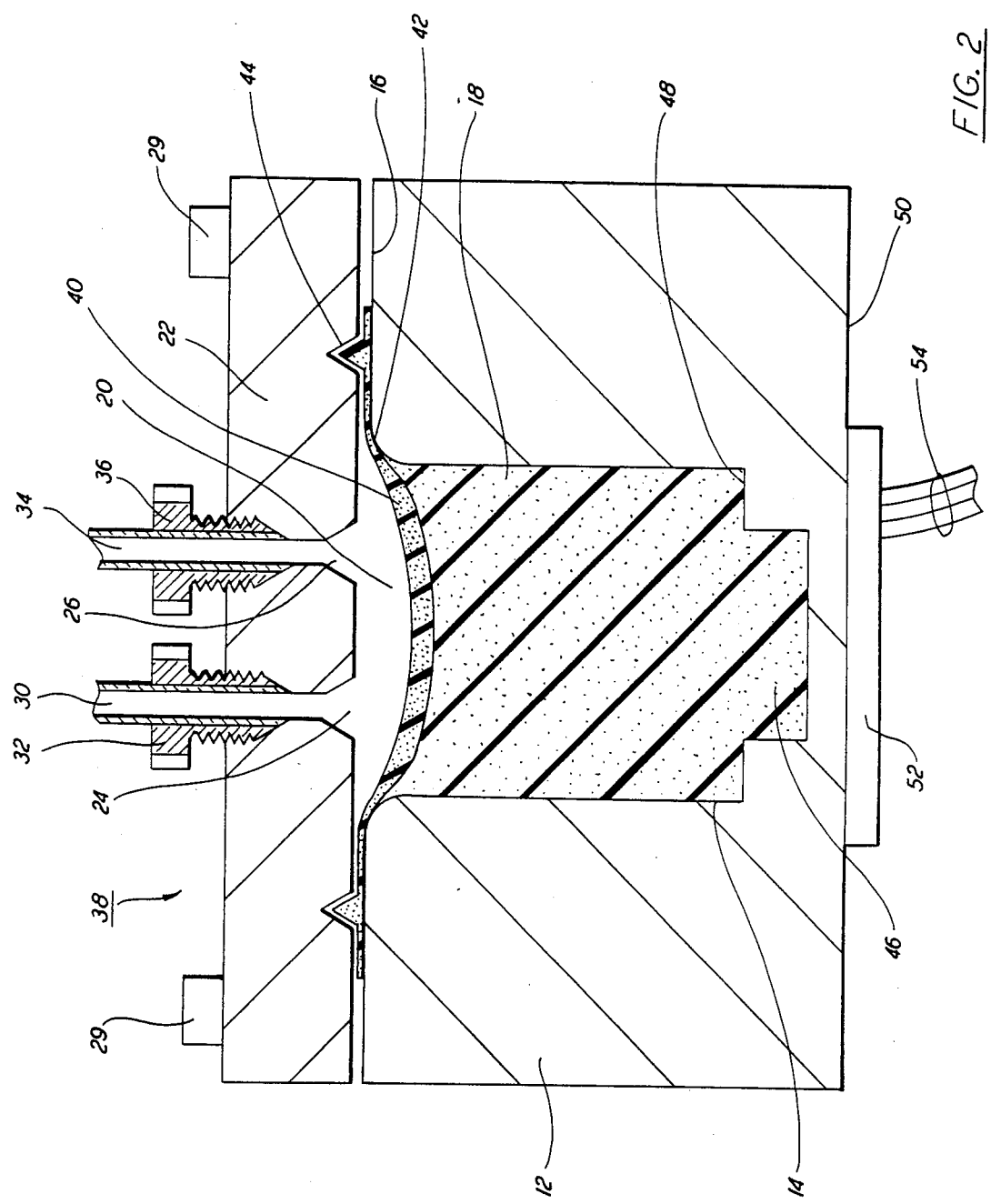
FIG. 2, which is a cross-sectional view of another pulse damper embodying the principles of the present invention.

Although the above-described pulse damper assembly 10 exhibits numerous advantages over conventional pulse dampers its use is limited. Specifically, the use of the pulse damper assembly 10 is limited to those analyses in which the solvent is chemically inactive with the compliant medium 18. In general, such analyses would be performed employing water as a solvent. A pulse damper assembly 38 is shown in FIG. 2 which overcomes this limitation.

For the convenience of the reader, all elements in the assembly 38 corresponding to elements in the assembly 10 are designated by the previously used numerals.

As shown, the preferred assembly 38 includes a housing 12 defining a cavity 14 containing an elastomeric compliant medium 18 and a cover 22 having solvent inlet and outlet means, 24 and 26 respectively.

The assembly 38 further includes a diaphragm 40 overlying and in contact with the compliant medium 18. Preferably, the diaphragm 40 is formed from a material, such as PTFE, which is chemically inert to solvents used in liquid chromatography.

To accommodate the diaphragm 40 the cavity 14 includes a curved rim 42 at the surface 16. Preferably, the rim 42 has a radius of curvature of about 1.8 millimeter. In addition, in order to maintain the desired solvent flow volume 20 the compliant medium 18 is formed with a plano-convex lens having a radius of curvature of about 15 cm. Preferably, the diaphragm 40 has an uncompressed thickness of about 250 micrometer.

Preferably the diaphragm 40 extends over the first surface 16 of the housing 12 and is secured in place by the cover 22 thereby eliminating the need for the gasket 28. Preferably, in this embodiment, the cover 22 includes an annular notch 44 having a diameter greater than the diameter of the cavity 14 and overlying the first surface 16. Thus, upon securing the cover 22 to the housing 12 the diaphragm 40 extrudes into the notch 44 and thereby relieves the radial tension of the diaphragm 40 created during tightening of the bolts 29.

The assembly 38 can be easily modified to provide a solvent pressure monitoring feature. In this embodiment, a section 46 of the bottom 48 of the cavity 14 is extended toward the bottom surface 50 of the housing 12. A strain gauge 52, having leads 54, is affixed to the bottom surface 50 beneath the section 46. By connecting the leads 54 to a conventional bridge circuit (not shown in the drawing), or the like, the pressure stored in the compliant medium 18 can be monitored. This stored pressure is directly related to the solvent pressure. One such strain gauge is the EA-13-455JB-350 manufactured and marketed by Measurements Group Inc.

Figure 3:
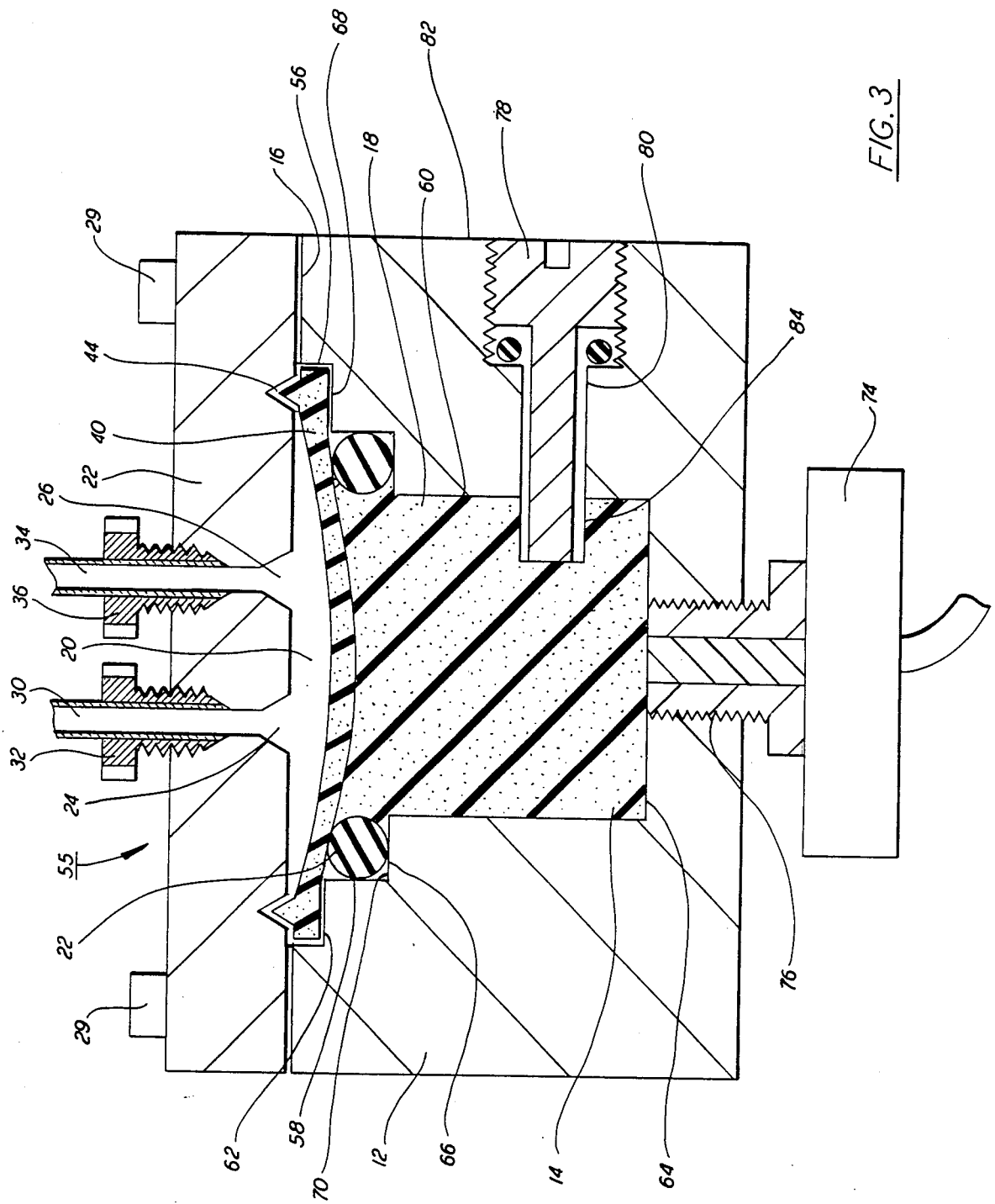
FIG. 3, which is a cross-sectional view of yet another pulse damper embodying the principles of the present invention.

A third embodiment, embodying the principles of the present invention and encompassing other options and modifications is designated at 55 in FIG. 3. As before, those elements previously identified in the FIG. 1 and 2 embodiments are designated by the same numerals in FIG. 3.

In this embodiment, the assembly 55 includes the cavity 14 having three concentric sections, 56, 58 and 60 which have circular cross-sections. The first section 56 is proximate the surface 16 and has a comparatively larger diameter. The second section 58 extends inwardly from the bottom 62 of the first section 56 and has a comparatively smaller diameter than the first section 56 but a comparatively larger diameter than the third section 60. The third section 60 has a bottom 64 and extends into the housing 12 from the bottom 66 of the second section 58. A first shelf 68 is formed in the plane of the transition from the first section 56 to the second section 58 and a second shelf 70 is formed in the plane of the transition from the second section 58 to the third section 60.

In this embodiment, the diaphragm 40 is formed from PTFE and nominally has an uncompressed thickness of about 250 micrometers whereas the first shelf 68 has a depth, measured perpendicularly from the first surface 16 of, on the order of about 200 micrometers. Consequently, the extruded thickness, i.e., 50 micrometers, extends into the annular notch 44 in the cover 22. Further, an O-ring is positioned on the second shelf 70 to support that portion of the diaphragm 40 extending thereacross.

In this embodiment, a pressure transducer 74 is positioned through an opening 76 in the bottom 50 of the housing 12 whereby the diaphragm of the pressure transducer 74 contacts the compliant medium 18 at the bottom 40 of the cavity 14. By use of such a pressure transducer the solvent pressure can be monitored and either removed or reduced should the pressure in the solvent clearance volume 20 become excessive.

Another feature which can be optionally included in the assemblies 10, 38 or 53, is the inclusion of a shipping plug 78. The shipping plug 78 is threaded into an opening 80 in the side wall 82 of the housing 12 and extends into the compliant medium 18. During shipment, where temperatures may be high, for example about 60° C., the shipping plug 78 would be unscrewed so that it does not extend into the compliant material 18. The gap 84 formed by the projection of the shipping plug 78 into the compliant medium 18 when backed out, causes the solvent clearance volume 20 to increase without requiring the compliant medium 18 to flow around any corner. In addition, the compliant medium 18 in contact with the shipping plug 78 dampens any vibrations caused during the shipping and thereby prevents the shipping plug 78 from loosening further and actually falling out.

The assemblies described herein have numerous advantages over conventional pulse dampers. For example, the compliant medium provides a completely adequate bulk modulus to absorb the pressure variations in known solvent pumping systems. Further, it is rather forgiving regarding leaks, i.e., it does not leak quickly or rapidly, if at all. Still further, it can be very easily molded to create a very precise solvent clearance volume. In addition, the assembly 10 is compatible with standard O-rings and therefore permits the use of a lightweight inexpensive aluminum housing. Further, although a shipping seal is not necessary, if one is used there is little concern regarding loss of the compliant medium thereacross and therefore the need for exacting an expensive seal is eliminated. Further, such a pulse damper has damping characteristics which remove the possibility of shock wave punchthrough, i.e., shockwaves caused by a rapid decrease in pressure. In addition, in the event that there is a rupture of the diaphragm, the replacement of the PTFE diaphragm is simple and can be performed by the purchaser rather than requiring the return of the pulse damper to the manufacturer.

The present invention has been described by use of specific embodiment which are exemplary only and which are not deemed to be limiting. Thus the present invention is limited only by the appended claims and the reasonable interpretation thereof.

What is claimed is:

1. A pulse damper for use in a liquid chromatographic system comprising, in combination:
    a housing having a cavity therein;
    a compliant elastomer material disposed in and substantially filling said cavity;
    a cover disposed and shaped to completely overlie said cavity;
    a diaphragm made of a flexible chemically inert material disposed between said housing and said cover;
    said cover and said elastomer being shaped to form a flow volume disposed between said cover and said diaphragm;
    means to secure said diaphragm and said cover to said housing;
    an inlet conduit and an outlet conduit each communicating with said flow volume, said inlet conduit, said flow volume and said outlet conduit providing a continuous path through which the fluid in the liquid chromatographic system can flow.

2. Pulse damper as claimed in claim 1 further comprising:
    a compressible gasket, said gasket being positioned between said housing and said cover.

3. Pulse damper as claimed in claim 2 further comprising:
    means for sensing the pressure stored in said compliant medium.

4. Pulse damper as claimed in claim 3 wherein:
    said cover includes a notch, said notch being annularly formed in said cover and overlying said one surface of said housing whereby said diaphragm extrudes thereinto thereby relieving radial forces therein.

5. Pulse damper as claimed in claim 1 further comprising:
    means for sensing the pressure stored in said compliant medium.

6. Pulse damper as claimed in claim 5 wherein said pressure sensing means is a strain gauge affixed to the bottom of said housing.

7. Pulse damper is claimed in claim 5 wherein said pressure sensing means is a pressure transducer having a diaphragm, which diaphragm contacts said compliant medium.

8. Pulse damper as claimed in claim 1 wherein said cavity includes:
    a first section terminating at said one surface and extending into said housing;
    a second section, said second section being concentric with said first section and having a diameter comparatively smaller than said first section, a first shelf being defined in the plane defined by the intersection of said first and said second section; and
    a third section, said third section being concentric with said second section and having a diameter comparatively smaller than said second section, a second shelf being defined in the plane defined by the intersection of said second and said third sections.

9. Pulse damper as claimed in claim 8 further comprising:
    an O-ring overlying said second shelf.

10. Pulse damper as claimed in claim 9 wherein:
    said diaphragm overlies said first shelf and contacts said O-ring.

11. Pulse damper as claimed in claim 1 further comprising:
    a removable shipping plug, said shipping plug penetrating said housing and extending into said compliant medium.

12. Pulse damper as claimed in claim 1 wherein said solvent flow volume is about 825 microliters.

13. The pulse damper of claim 1 wherein:
    said cover includes a notch, said notch being annularly formed in said cover.

* * * * *